(12) United States Patent
Buxton et al.

(10) Patent No.: US 8,565,847 B2
(45) Date of Patent: Oct. 22, 2013

(54) EVALUATION BOARD FOR A MEDICAL MONITORING MODULE SYSTEM AND METHOD

(75) Inventors: Kip Buxton, Arvada, CO (US); Randy Doyal, Lyons, CO (US); David Orian, Tracy, CA (US); Tom Wilmering, Westminister, CO (US)

(73) Assignee: Covidien LP, Mansfield, MA (US)

( * ) Notice: Subject to any disclaimer, the term of this patent is extended or adjusted under 35 U.S.C. 154(b) by 696 days.

(21) Appl. No.: 12/725,218

(22) Filed: Mar. 16, 2010

(65) Prior Publication Data

US 2011/0077488 A1  Mar. 31, 2011

Related U.S. Application Data

(60) Provisional application No. 61/247,226, filed on Sep. 30, 2009.

(51) Int. Cl.
*A61B 5/00* (2006.01)

(52) U.S. Cl.
USPC .......................................... 600/324; 600/112

(58) Field of Classification Search
USPC ................................................ 600/324, 112
See application file for complete search history.

(56) References Cited

U.S. PATENT DOCUMENTS

| | | |
|---|---|---|
| 5,058,588 A | 10/1991 | Kaestle |
| 5,347,524 A | 9/1994 | I'Anson et al. |
| 5,371,692 A | 12/1994 | Draeger et al. |
| 5,375,604 A | 12/1994 | Kelly et al. |
| 5,759,199 A | 6/1998 | Snell et al. |
| 5,783,821 A | 7/1998 | Costello, Jr. |
| 5,862,803 A | 1/1999 | Besson et al. |
| 5,957,854 A | 9/1999 | Besson et al. |
| RE36,620 E | 3/2000 | Costello, Jr. |
| 6,289,238 B1 | 9/2001 | Besson et al. |
| RE37,970 E | 1/2003 | Costello, Jr. |
| 6,577,893 B1 | 6/2003 | Besson et al. |
| 6,584,336 B1 | 6/2003 | Ali et al. |
| 6,593,763 B2 | 7/2003 | Weber |
| 6,770,028 B1 | 8/2004 | Ali et al. |

(Continued)

FOREIGN PATENT DOCUMENTS

| | | |
|---|---|---|
| DE | 69123448 | 5/1997 |
| WO | WO9200513 | 1/1992 |
| WO | WO9309711 | 5/1993 |

OTHER PUBLICATIONS

PCT International Search Report, Applicant's File Reference: H-RM-01797WO, International Application No. PCT/US2010/042624, Applicant: Nellcor Puritan Bennett LLC, Date of Mailing: Nov. 30, 2010, International Filing Date: Jul. 20, 2010.

(Continued)

*Primary Examiner* — Clayton E LaBalle
*Assistant Examiner* — Linda B Smith
(74) *Attorney, Agent, or Firm* — Fletcher Yoder PC

(57) ABSTRACT

An evaluation board for a medical monitoring module is provided. The evaluation board includes a socket configured to receive a medical monitoring module and a plurality of connections for connection to a host or host simulator and a second device. The evaluation board may include a non-isolated power supply to provide power to the medical monitoring module. The evaluation board may also provide communication in a protocol between the host or host simulator and the medical monitoring module.

20 Claims, 12 Drawing Sheets

(56) References Cited

U.S. PATENT DOCUMENTS

| | | | |
|---|---|---|---|
| 6,850,788 | B2 | 2/2005 | Al-Ali |
| 6,954,664 | B2 | 10/2005 | Sweitzer et al. |
| 6,993,371 | B2 | 1/2006 | Kiani et al. |
| 7,017,097 | B1 | 3/2006 | Moore et al. |
| 7,215,991 | B2 | 5/2007 | Besson et al. |
| 7,316,648 | B2 | 1/2008 | Kelly et al. |
| 7,346,378 | B2 | 3/2008 | Ruiter |
| 7,377,794 | B2 | 5/2008 | Al-Ali et al. |
| 7,428,432 | B2 | 9/2008 | Ali et al. |
| 7,500,950 | B2 | 3/2009 | Al-Ali et al. |
| 7,530,949 | B2 | 5/2009 | Al Ali et al. |
| 7,621,877 | B2 | 11/2009 | Schnall |
| 2002/0138017 | A1* | 9/2002 | Bui et al. .................. 600/537 |
| 2002/0161291 | A1 | 10/2002 | Kianl et al. |
| 2003/0197679 | A1 | 10/2003 | Ali et al. |
| 2004/0186357 | A1 | 9/2004 | Soderberg et al. |
| 2004/0189281 | A1 | 9/2004 | Le et al. |
| 2005/0065417 | A1 | 3/2005 | Ali et al. |
| 2005/0288571 | A1 | 12/2005 | Perkins et al. |
| 2006/0094936 | A1* | 5/2006 | Russ ......................... 600/300 |
| 2006/0155589 | A1 | 7/2006 | Lane et al. |
| 2006/0211923 | A1 | 9/2006 | Al-Ali et al. |
| 2006/0211932 | A1 | 9/2006 | Al-Ali et al. |
| 2006/0226992 | A1 | 10/2006 | Al-Ali et al. |
| 2006/0258926 | A1 | 11/2006 | Ali et al. |
| 2007/0005118 | A1 | 1/2007 | Carter et al. |
| 2007/0180140 | A1 | 8/2007 | Welch et al. |
| 2007/0208235 | A1 | 9/2007 | Besson et al. |
| 2008/0039701 | A1 | 2/2008 | Ali et al. |
| 2008/0091092 | A1* | 4/2008 | Al-Ali ....................... 600/310 |
| 2008/0108884 | A1 | 5/2008 | Kiani |
| 2009/0105983 | A1 | 4/2009 | Variyam et al. |
| 2009/0150484 | A1 | 6/2009 | Roberts |
| 2009/0158274 | A1 | 6/2009 | Roberts |
| 2009/0177249 | A1 | 7/2009 | Roberts et al. |
| 2009/0177769 | A1 | 7/2009 | Roberts |
| 2009/0221887 | A1 | 9/2009 | Mannheimer et al. |
| 2009/0234208 | A1 | 9/2009 | Al-Ali et al. |
| 2011/0077487 | A1 | 3/2011 | Buxton et al. |
| 2011/0078596 | A1 | 3/2011 | Rawlins et al. |

OTHER PUBLICATIONS

Buschman, J.P., et al.; "Principles and Problems of Calibration of Fetal Oximeters," *Biomedizinische Technik*, vol. 42, pp. 265-266 (1997).

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

East, Christine E., et al.; "Fetal Oxygen Saturation and Uterine Contractions During Labor," *American Journal of Perinatology*, vol. 15, No. 6, pp. 345-349 (Jun. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engie in Medicine and Biology Society*, vol. 20, No. 6, p. 3072-3075 (1998).

Such, Hans Olaf; "Optoelectronic Non-invasive Vascular Diagnostics Using multiple Wavelength and Imaging Approach," *Dissertation*, (1998).

Todd, Bryan, et al.; "The Identification of Peaks in Physiological Signals," *Computers and Biomedical Research*, vol. 32, pp. 322-335 (1999).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, pp. 1018-1026 (Aug. 2000).

Kaestle, S.; "Determining Artefact Sensitivity of New Pulse Oximeters in Laboratory Using Signals Obtained from Patient," *Biomedizinische Technik*, vol. 45 (2000).

Cysewska-Sobusaik, Anna; "Metrological Problems With noninvasive Transillumination of Living Tissues," *Proceedings of SPIE*, vol. 4515, pp. 15-24 (2001).

Belal, Suliman Yousef, et al.; "A fuzzy system for detecting distorted plethysmogram pulses in neonates and paediatric patients," *Physiol. Meas.*, vol. 22, pp. 397-412 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Relente, A.R., et al.; "Characterization and Adaptive Filtering of Motion Artifacts in Pulse Oximetry using Accelerometers," *Proceedings of the Second joint EMBS/BMES Conference*, Houston, Texas, pp. 1769-1770 (Oct. 23-26, 2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, pp. 469 (2002).

Chan, K.W., et al.; "17.3: Adaptive Reduction of Motion Artifact from Photoplethysmographic Recordings using a Variable Step-Size LMS Filter," IEEE, pp. 1343-1346 (2002).

Stetson, Paul F.; "Determining Heart Rate from Noisey Pulse Oximeter Signals Using Fuzzy Logic," *The IEEE International Conference on Fuzzy Systems*, St. Louis, Missouri; pp. 1053-1058 (May 25-28, 2003).

Cyrill, D., et al.; "Adaptive Comb Filter for Quasi-Periodic Physiologic Signals," *Proceedings of the 25th Annual International Conference of the IEEE EMBS*, Cancun, Mexico; pp. 2439-2442 (Sep. 17-21, 2003).

Lee, C.M., et al.; "Reduction of motion artifacts from photoplethysmographic recordings using wavelet denoising approach," *IEEE EMBS Asian-Pacific Conference on Biomedical Engineering*, pp. 194-195 (Oct. 20-22, 2003).

Johansson, A.; "Neural network for photoplethysmographic respiratory rate monitoring," *Medical & Biological Engineering & Computing*, vol. 41, pp. 242-248 (2003).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy; pp. 718-723 (May 18-20, 2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

www.clinicaldynamics.com; SmartSat™ Pulsometer Oximetry Analyzer "The Gold Standard in Oximetry Testing" 2 pages (2008).

Kim, J.M., et al.; "Signal Processing Using Fourier & Wavelet Transform," pp. II-310-II-311 (undated).

Hamilton, Patrick S., et al.; "Effect of Adaptive Motion-Artifact Reduction on QRS Detection," *Biomedical Instrumentation & Technology*, pp. 197-202 (undated).

Huang, J. et al.; "Low Power Motion Tolerant Pulse Oximetry," *Abstracts*, A7, p. S103. (undated).

Neumann, R. et al.; "Fourier Artifact suppression Technology Provides Reliable $SpO_2$," *Abstracts*, A11, p. S105 (undated).

Odagiri, Y.; "Pulse Wave Measuring Device," *Micromechatronics*, vol. 42, No. 3, pp. 6-11 (Article in Japanese—contains English summary of article) (undated).

* cited by examiner

EVALUATION BOARD FOR A MEDICAL MONITORING MODULE SYSTEM AND METHOD

RELATED APPLICATION

This application claims the benefit of U.S. Provisional Application No. 61/247,226 filed Sep. 30, 2009, which application is hereby incorporated herein by reference.

BACKGROUND

The present disclosure relates generally to medical monitoring systems, and more particularly, to testing and integration of medical monitoring modules with medical monitors.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological parameters of their patients. A medical monitoring system may include a monitor that receives signals from various types of optical, electrical, and acoustic sensors. These monitors may display various physiological parameters to a caregiver via a display. In some instances, the sensors and any corresponding hardware may be manufactured by a single manufacturer and may communicate over a proprietary protocol. Additionally, designing a medical monitor that is operative with such sensors, corresponding hardware, and protocols may be challenging. The medical monitor may not provide the signal processing, power, or other features expected by the sensor and corresponding hardware. Additionally, monitoring and testing of the various devices may not be easily performed.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
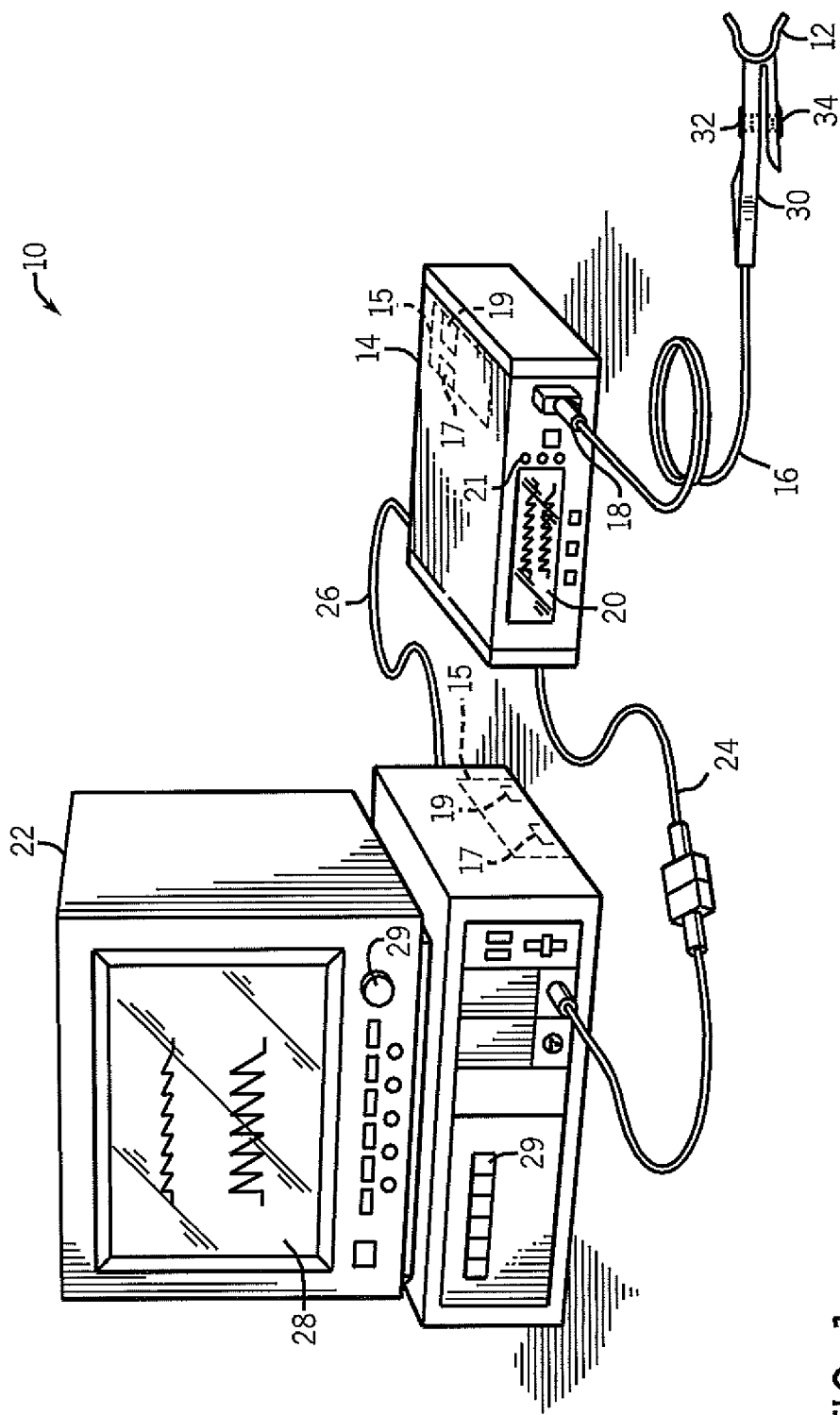
FIG. 1 depicts a medical monitoring system in accordance with an embodiment of the present disclosure.

FIG. 1 depicts a medical monitoring system 10 having a sensor 12 coupled to a monitor 14 in accordance with an embodiment of the present disclosure. The sensor 12 may be coupled to the monitor 14 via sensor cable 16 and sensor connector 18, or the sensor 12 may be coupled to a transmission device (not shown) to facilitate wireless transmission between the sensor 12 and the monitor 14. The monitor 14 may be any suitable monitor, such as those available from Nellcor Puritan Bennett, LLC. The monitor 14 may be configured to calculate physiological parameters from signals received from the sensor 12 when the sensor 12 is placed on a patient. In some embodiments, the monitor 14 may be primarily configured to determine, for example blood and/or tissue oxygenation and perfusion, respiratory rate, respiratory effort, continuous non-invasive blood pressure, cardiovascular effort, glucose levels, level of consciousness, total hematocrit, hydration, electrocardiography, temperature, or any other suitable physiological parameter. To enable this functionality, the monitor 14 may include a medical monitoring module 15 that communicates with the sensor 12 and outputs information based on data received from the sensor 12. The module 15 may be a printed circuit board assembly having one or processors 17 and/or memory 19. The memory 19 may include volatile memory (e.g., RAM) and non-volatile memory (e.g., ROM, flash memory, etc.) For example, in one embodiment, the monitor 14 may be a pulse oximetry monitor and the module 15 may be a pulse oximetry module that is/may be configured to provide oxygen saturation (SpO2), pulse rate, pulse waveform and pulse amplitude modulation (also referred to as "Blip"), interference indicators, sensor disconnect indicators, sensor off patient indicators, sensor adjust messages, alarm management, and/or analog outputs, In such an embodiment, the monitor 14 may be a monitor manufactured by Nellcor Puritan Bennett, LLC, and the medical monitoring module 15 may be a NELL-1, NELL-2, or NELL-3 pulse oximetry module available from Nellcor Puritan Bennett, LLC. Additionally, the monitor 14 may include a display 20 configured to display information regarding the physiological parameters, information about the system, and/or alarm indications. The monitor 14 may include various input components 21, such as knobs, switches, keys and keypads, buttons, etc., to provide for operation and configuration of the monitor.

Furthermore, to upgrade conventional operation provided by the monitor 14 to provide additional functions, the monitor 14 may be coupled to a multi-parameter patient monitor 22 via a cable 24 connected to a sensor input port or via a cable 26 connected to a digital communication port. In addition to the monitor 14, or alternatively, the multi-parameter patient monitor 22 may be configured to calculate physiological parameters and to provide a central display 28 for information from the monitor 14 and from other medical monitoring devices or systems. In some embodiments, the monitor 22 may be primarily configured to display and/or determine, for example blood and/or tissue oxygenation and perfusion, respiratory rate, respiratory effort, continuous non-invasive blood pressure, cardiovascular effort, glucose levels, level of consciousness, total hematocrit, hydration, electrocardiography, temperature, or any other suitable physiological parameter. To enable this functionality, the monitor 22 may additionally, or alternatively, include the medical monitoring module 15 that communicates with the sensor 12 (and/or monitor 14) and outputs information based on data received from the sensor 12 (and/or monitor 14). The monitor 22 may include a slot, socket, or other receptacle configured to receive the medical monitoring module 15. In other embodiments, the medical monitoring module 15 or the components thereof may be physically and electronically integrated with a circuit board or other electronic component of the monitor 22. In one embodiment, the module 15 may be a pulse oximetry module that is may be configured to provide oxygen saturation (SpO2), pulse rate, pulse waveform and pulse amplitude modulation (also referred to as "Blip"), interference indicators, sensor disconnect indicators, sensor off patient indicators, sensor adjust messages, alarm management, and/or analog outputs to the monitor 22. For example, the multi-parameter patient monitor 22 may be configured to display an SpO2 signal (such as a plethysmographic waveform) on the display 28. In such an embodiment, the medical monitoring module 15 may be a NELL-1, NELL-2, or NELL-3 pulse oximetry module available from Nellcor Puritan Bennett, LLC. The monitor may include various input components 29, such as knobs, switches, keys and keypads, buttons, etc., to provide for operation and configuration of the monitor 22. In addition, the monitor 14 and/or the multi-parameter patient monitor 22 may be connected to a network to enable the sharing of information with servers or other workstations.

In some embodiments, the multi-parameter patient monitor 22 having the medical monitoring module 15 may be directly connected to the sensor 12. In such an embodiment, the system 10 may not include the monitor 14 and may rely on direct communication between the multi-parameter patient module 22 and the module 15. As discussed further below, monitoring, testing, and debugging of the module 15 (and communication to and from the module 15), either as a standalone module or when installed or integrated into the monitor 22, may be performed using the system and techniques described herein.

The sensor 12 may be any sensor suitable for detection of any physiological parameter. The sensor 12 may include optical components (e.g., one or more emitters and detectors), acoustic transducers or microphones, electrodes for measuring electrical activity or potentials (such as for electrocardiography), pressure sensors, motion sensors, temperature sensors, etc. In one embodiment, the sensor 12 may be configured for photo-electric detection of blood and tissue constituents. For example, the sensor 12 may be a pulse oximetry sensor such as those available from Nellcor-Puritan Bennett. As shown in FIG. 1, the sensor 12 may be a clip-type sensor suitable for placement on an appendage of a patient, e.g., a digit, an ear, etc. In other embodiments may be a bandage-type sensor having a generally flexible sensor body to enable conformable application of the sensor 12 to a sensor site on a patient. In yet other embodiments, the sensor 12 may be secured to a patient via adhesive (e.g., in an embodiment having an electrode sensor) on the underside of the sensor body or by an external device such as headband or other elastic tension device. In yet other embodiments, the sensor 12 may be configurable sensors capable of being configured or modified for placement at different sites (e.g., multiple tissue sites such as a digit, a patient's forehead, etc.).

In one embodiment, the sensor 12 may include a sensor body 30 having an emitter 32 for emitting light at certain wavelengths into a patient's tissue and a detector 34 for detecting the light after it is reflected and/or absorbed by the patient's blood and/or tissue. In such an embodiment where the sensor 12 is a pulse oximetry sensor or other photo-electric sensor, the emitter 32 may be configured to emit one or more wavelengths of light, e.g., red and infrared (IR), such as through LED's or other light sources. The detector 34 may include photo-detectors for detecting the wavelengths of light reflected or transmitted through blood or tissue constituents of a patient and converting the intensity of the received light into an electrical signal.

The module 15 may communicate with the sensor 12 over a proprietary interface and/or protocol. Additionally, the monitor 14 (and monitor 22) may communicate with the module 15 over an identical or different proprietary protocol, such that messages sent between the module 15 and other devices may be formatted according to a proprietary protocol. To enable this functionality, the module 15 may include hardware and software components to implement the proprietary interfaces and/or protocols. In one embodiment, the protocol implemented by the module 15 may by the Standard Host Interface Protocol (SHIP) developed by Nellcor Puritan Bennett, LLC. In such embodiments, design, debug, and testing of a monitor to ensure operability with the sensor 12 and/or the corresponding module 15 may be difficult. Additionally, monitoring, testing, and debugging interaction of devices with the proprietary protocol may not be easily performed due to the proprietary nature of the protocol.

As described further below, embodiments of the present disclosure include a kit that provides hardware and software to enable monitor, debug, and testing of devices operable with a proprietary module and corresponding protocol. Such device may include a medical monitor (also referred to as a "host") configured to receive data from a sensor or other device operable with the module. The kit may enable easier integration of the module with host and ensure that the host can interpret and display data received from the module.

The kit may provide display and interpretation of operation of the module and any communication between the module and a host. The kit may include connections to a sensor device (e.g., a sensor or a sensor simulator) and a host or a host simulator. In this manner, design, debug, and testing may progress from a host simulator to hardware implementation of the host and the module 15.

Figure 2:
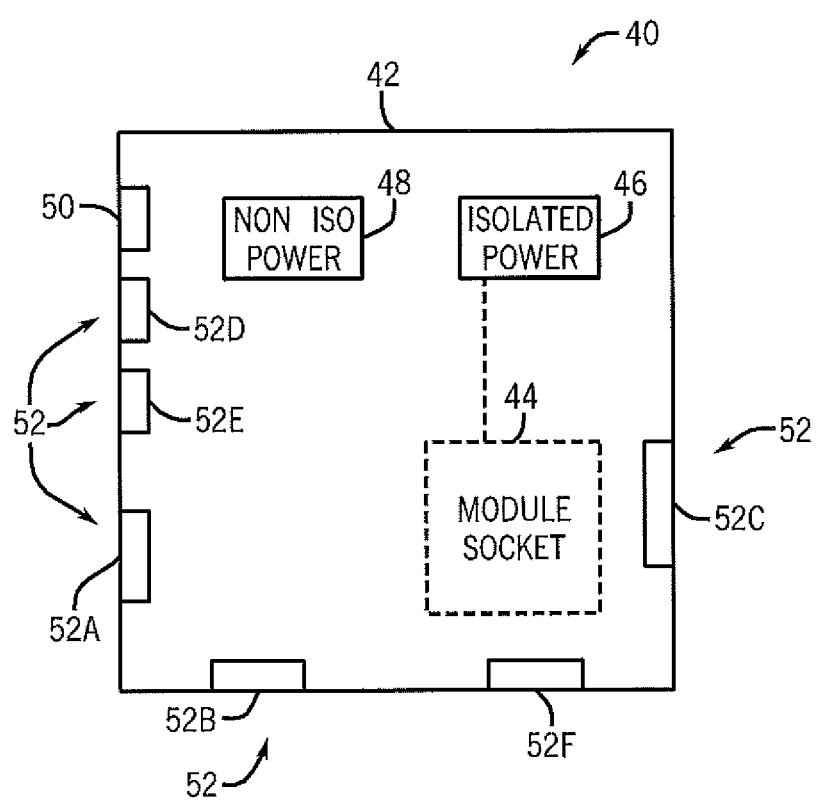
FIG. 2 is a schematic of an evaluation board for a monitoring, testing and debugging system in accordance with an embodiment of the present disclosure.

As mentioned above, the kit may include hardware that enables connection and operation of the module for monitoring and testing. FIG. 2 depicts an evaluation board 40 that provides for connection of the module 15, a host, a computer, and other components of a monitoring, debugging, and testing system. The evaluation board 40 may be a printed circuit board assembly 42 that may include a module socket 44, isolated power supply 46, non-isolated power supply 48, a power connection 50, and various other connections 52.

During operation of the evaluation board, the module 15 may be installed in the module socket 44. The module socket 44 provides a connection to the module to enable transfer of data over one or more of the connections 52. Additionally, the module socket 44 may provide power from the isolated power supply 46 to the module 44. The isolated power supply 46 may receive power from the power connection 50 and may include an AC to DC converter and may meet any requirements of a medial grade isolated power supply, thus providing accurate power emulation of a medical device having the module. In one embodiment, the isolated power supply 46 may have a leakage current of less than 100 uA at 1500 VAC and may include an isolation barrier between the a non-isolated ground and the isolated ground of greater than 0.190 inches. The non-isolated power supply 48 may receive power from the power connection 50 and may include an AC to DC converter and may provide the evaluation board 40 with DC input power. In one embodiment, the input power may be between 7V and 8V and provide at least 600 mA. The non-isolated power supply 48 may provide DC power to the connectors 52.

The connections 52 may include any number and type of connections to the enable control and monitoring of the evaluation board 40 and any module installed in the evaluation board 40. For example, in one embodiment, the connections 52 may include a Universal Serial Bus (USB) connection 52A, a sensor cable connection 5211, a serial communications port 52C, an ECG input port 52D, and an analog output 52E. In some embodiments, the ECG input port 52D may provide a module coupled to the evaluation board 40 with C-LOCK® ECG synchronization. The evaluation board 40 may also include an additional "pick-off" connection 52F to enable monitoring of a hardware host (such as a medical monitor). It should be appreciated that other embodiments may include any number and combination of the connections described above and may include any other suitable connections.

In some embodiment, the USB connection may provide for connection to one or more serial ports (e.g., USB-serial) on the evaluation board 40. These additional serial ports may allow for communication to and from a module installed in the module socket 44. The serial port 52C and other serial ports may use the same circuitry, but communication over one or more ports may be routed by on-board switches on the evaluation board 40 to prevent message collisions.

Figure 3:
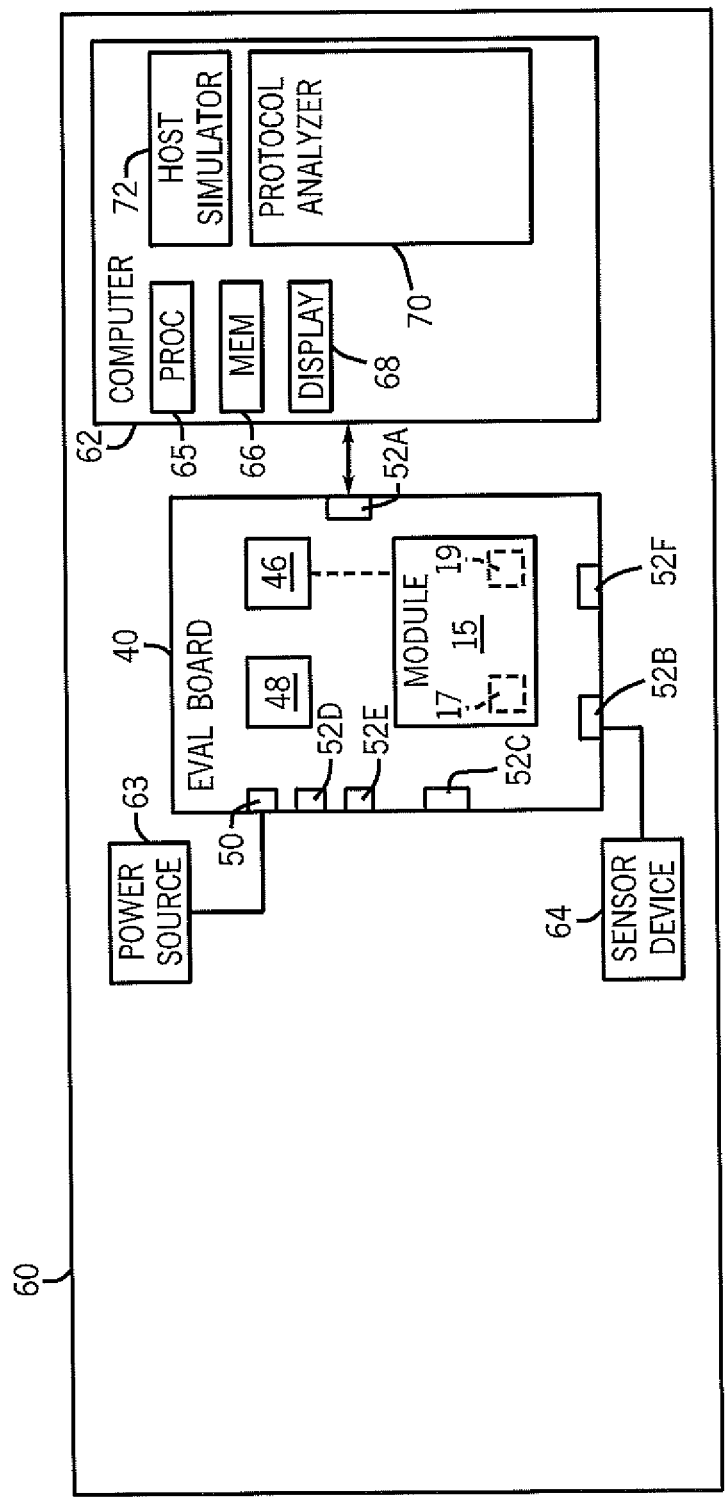
FIG. 3 is a schematic of a first configuration of a monitoring, testing, and debugging system having the evaluation board of FIG. 2 and a medical monitoring module in accordance with an embodiment of the present disclosure.
Figure 4:
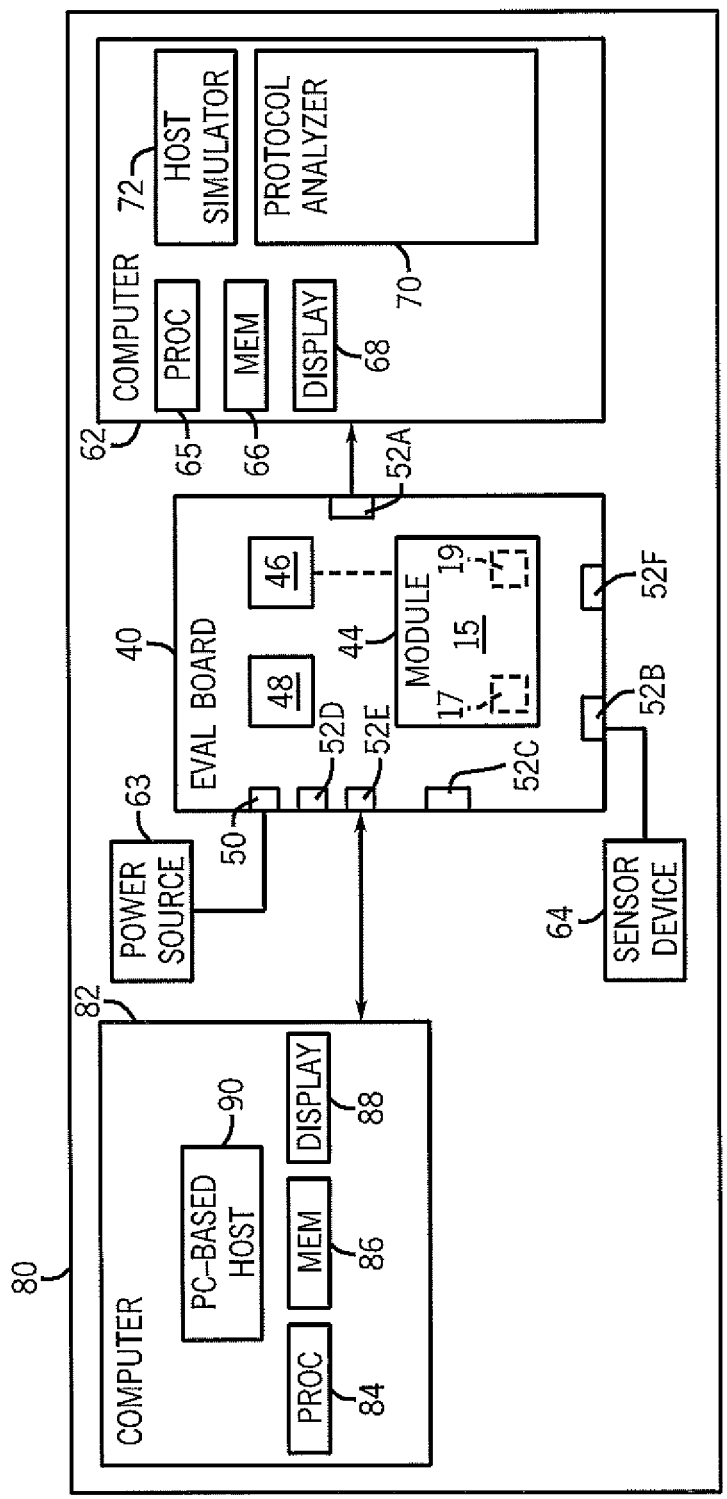
FIG. 4 is a schematic of a second configuration of a monitoring, testing, and debugging system having the evaluation board of FIG. 2 and a medical monitoring module in accordance with an embodiment of the present disclosure.
Figure 5:
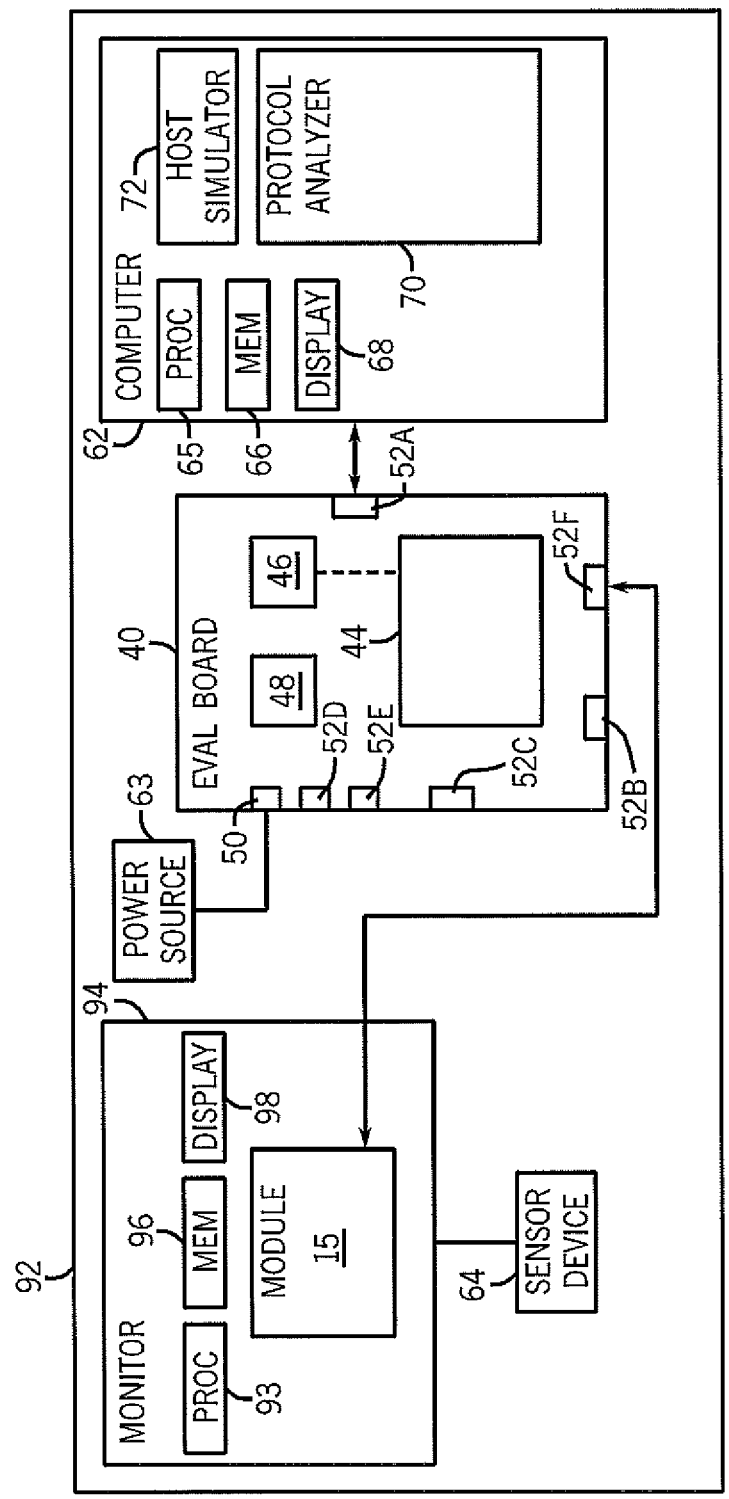
FIG. 5 is a schematic of a third configuration of a monitoring, testing, and debugging system having the evaluation board of FIG. 2 and a medical monitoring module in accordance with an embodiment of the present disclosure.

FIGS. 3-5 depict various system configurations of the evaluation board 40 and other components of a design and testing system to evaluate operation of a host and the module 15. Each configuration may include use of a sensor device coupled to the evaluation board 40. Additionally, some configurations may include use of a host simulator, a software host, or a hardware host (e.g., a medical monitor having an integrated module). Each configuration may include different types and numbers of devices coupled to the evaluation board 40.

FIG. 3 depicts a first system configuration 60 of the evaluation board 40 that includes a computer 62 (e.g., a personal computer such as a desktop, laptop, etc.) coupled to the evaluation board 40. In the first configuration, the module 15 may be coupled to the evaluation board 40 by the module socket 44. The evaluation board 40 may be coupled to a power source 63 (e.g., an AC power source, a power adapter coupled to an AC power source, a battery, etc.) The computer 62 may be coupled to the evaluation board 40 by the USB connection 52A. Alternatively, in some embodiments the computer 62 may be coupled to the evaluation board 40 by the serial communications port 52C.

The evaluation board 40 may also be coupled to a sensor device 64. In one embodiment, the sensor device 64 may be any suitable medical sensor, such as pulse oximetry sensor to enable monitoring of blood-oxygen saturation of a subject. In such an embodiment, the sensor device 64 may be a DS100A sensor, a Max-Fast® sensor, or a Softcare® sensor available from Nellcor Puritan Bennett, LLC. In other embodiments, the sensor device 64 may be a sensor simulator that simulates monitoring of a physiological parameter and provides data to the evaluation board 40 and the module 15. In such an embodiment, the sensor device 64 may be an SRC-MAX Portable Oximetry Tester available from Nellcor Puritan Bennett, LLC.

The computer 62 includes a processor 65, a memory 66, and a display 68. The memory 66 may include volatile memory (e.g., RAM) and non-volatile memory (e.g., flash memory, magnetic storage devices, etc). The computer 62 may include software (e.g., programs) to provide control and/or monitoring of the module 15 and the evaluation board 40. For example, the computer may include a protocol analyzer 70 configured to display, interpret, or otherwise process protocol messages. Additionally, as shown in FIG. 3, the first system configuration 60 may not include a hardware host or a software host. In such a configuration, the computer 62 may execute one or more programs that simulate a host. For example, as shown in FIG. 3, the computer 62 may include a host simulator 72. As described further below, the host simulator 72 simulates a host that communicates with the module 15, generates messages from the module according to the configurations and actions set in the host simulator 72, and displays data received from the module 15. The protocol analyzer 70 and the host simulator 72 may be programmed as executable code stored on a tangible machine readable medium (e.g., the memory 66) accessible by the computer 62. In some embodiments, the protocol analyzer 70 and the host simulator 72 may be encoded on a CD-ROM, diskette, flash drive, or other removable media.

In the first configuration depicted in FIG. 3, a user may monitor two-way communication between the module 15 and the host simulator 72 through the connection to the evaluation board 40. The communication received and sent by the module 15 may be in a specific protocol monitored by the protocol analyzer 70. The protocol analyzer 70 is configured to display protocol messages sent from the host simulator 72 to the module 15 and messages sent from the module 15 to the host simulator 72. The protocol analyzer 70 is configured to parse messages formatted according to the protocol used by the module 15.

Additionally, in some embodiments the protocol analyzer 70 may enable a user to send messages directly to the module 15 and monitor the response from the module 15. A user may also use the host simulator 72 to display the data from the sensor device 64 as interpreted by the module 15. Additionally, the user can set different parameters on the host simulator 72, such as display parameters, alarm settings, sampling rate, etc., and monitor how the module responds and communicates to such parameter settings. Further, a user may change the data provided by the sensor device 64 (such as by adjusting a sensor or sensor simulator) and monitor the communication between the module and the host simulator 72. In this manner, a user may evaluate the operation of the module, in response to different sensor device data or host settings, without a hardware or software host.

FIG. 4 depicts a second system configuration 80 of the evaluation board 40 that enables further development of devices operable with the module. In the second system configuration 80, the evaluation board 40 may be coupled to the computer 62 (e.g., a personal computer such as a desktop, laptop, etc.) that includes the protocol analyzer 70 and the host simulator 72, such as by the USB port 52A. Additionally, the evaluation board 40 may be coupled to the sensor device 64, such as a sensor configured to monitor a physiological parameter or a sensor simulator, by the sensor cable connector 52B. As mentioned above, in some embodiments the sensor may be pulse oximetry sensor and the module 15 may be a pulse oximetry module. The sensor device 64 may be coupled to the evaluation board 40 by a patient interface cable.

As shown in FIG. 4 a second computer 82 (e.g., a personal computer such as a desktop, laptop, etc., a server, or any other suitable computing device) may be coupled to the evaluation board, such as by the serial communication port 52C. The second computer 82 may include a processor 84, memory 86, and a display 88. The memory 86 may include volatile memory (e.g., RAM) and non-volatile memory (e.g., flash memory, magnetic storage device, etc). The second computer 82 may include a software host 90. The software host 90 may include some or all of the components of a hardware medical monitor. The hardware and software components of a hardware host may be emulated by executing the software host 90 on the second computer 82 to enable design, debug, and testing of such components. In some embodiments, as shown in FIG. 4, the computer 62 and the computer 82 may be different devices. In other embodiments, a single computer may be coupled to the evaluation board 40 and may execute the protocol analyzer 70, the host simulator 72, and the software host 90.

Using the protocol analyzer 70, a user may use the second system configuration 80 to monitor communication between the host 90 and the module 15 over the protocol used by the module 15. As described above, the protocol analyzer 70 can display the protocol messages on the computer 62. The evaluation board 40 provides routing of messages among the individual devices of the second system configuration 80. For example, a user may change the data provided by the sensor device 64 (such as by adjusting a sensor or sensor simulator) and monitor the communication between the module 15 and the host 90. Additionally, a user may change settings on the host 90 and monitor the communication to the module 15 and the response from the module 15. In some embodiments, a user may send messages to the module 15 and/or the host 90 from the protocol analyzer 70. Thus, a user may test and debug operability of the host 90 with the module 15, using the connections provided by the evaluation board 40 and the protocol analyzer 70.

FIG. 5 depicts a third system configuration 92 of the evaluation board 40 that may be used to evaluate operability of a hardware host, e.g., medical monitor 94 having the module 15 integrated into the monitor 94. In one embodiment, the medical monitor 94 may be a multi-parameter medical monitor. As discussed above, the computer 62 may be coupled to the evaluation board 40 by the USB port 52A. The computer 62 may include the protocol analyzer 70 and the host simulator 72 and may enable a user to configure and use the protocol analyzer 70 to monitor the communication to and from the module 15.

The medical monitor 94 may be coupled to the evaluation board 40 through any available connection 52. In one embodiment, the medical monitor 94 may be coupled to the evaluation board 40 by the pick-off connection 52F. In some embodiments, the medical monitor 94 may be coupled to both the serial port 52B and the pick-off connection 52F using a Y-cable having one end connected to the monitor 94 and two ends coupled to the evaluation board 40. The medical monitor 94 may include a processor 93, memory 96, and a display 98. The memory 96 may include volatile memory (e.g., RAM) and non-volatile memory (e.g., flash memory, magnetic storage device, etc). As shown in FIG. 5, the module 15 may be operably installed in the medical monitor 94 to provide the module functionality to the monitor 94. The medical monitor 94 may also be coupled to the sensor device 64, e.g., a sensor configured to monitor a physiological parameter or a sensor simulator. As mentioned above, in some embodiments, the sensor may be a pulse oximetry sensor and the module 15 may be a pulse oximetry module.

The medical monitor 94 may receive data from the sensor device 64 for processing by the module 15. The module 15 may provide output to the monitor 94 based on the sensor data and configuration settings of the monitor 94. The communication received and sent by the module 15 may be in a specific protocol monitored by the protocol analyzer 70. A user may view protocol messages between the module 15 and the medical monitor 94 using the protocol analyzer 70, so that the user may monitor, test, and debug the medical monitor 94 and its interaction with the module 15. Additionally, in some embodiments, the protocol analyzer 70 may provide for transmitting messages to the module 15 and/or the medical monitor 94 via the connections to the evaluation board 40. In this configuration 92, a user is able to test and debug a hardware host (monitor 94) that integrates the module 15 by monitoring the protocol messages communicated during operation of the host.

In should be appreciated that other embodiments may include alternate configurations to those illustrated above in FIGS. 3-5. Such configurations may include any combination of devices coupled to the evaluation board 40. Additionally, in other configurations the evaluation board may be coupled to an ECG sensor by the ECG input port 52G. In other embodiments, an analog device may be coupled to the analog output 52E.

Figure 6:
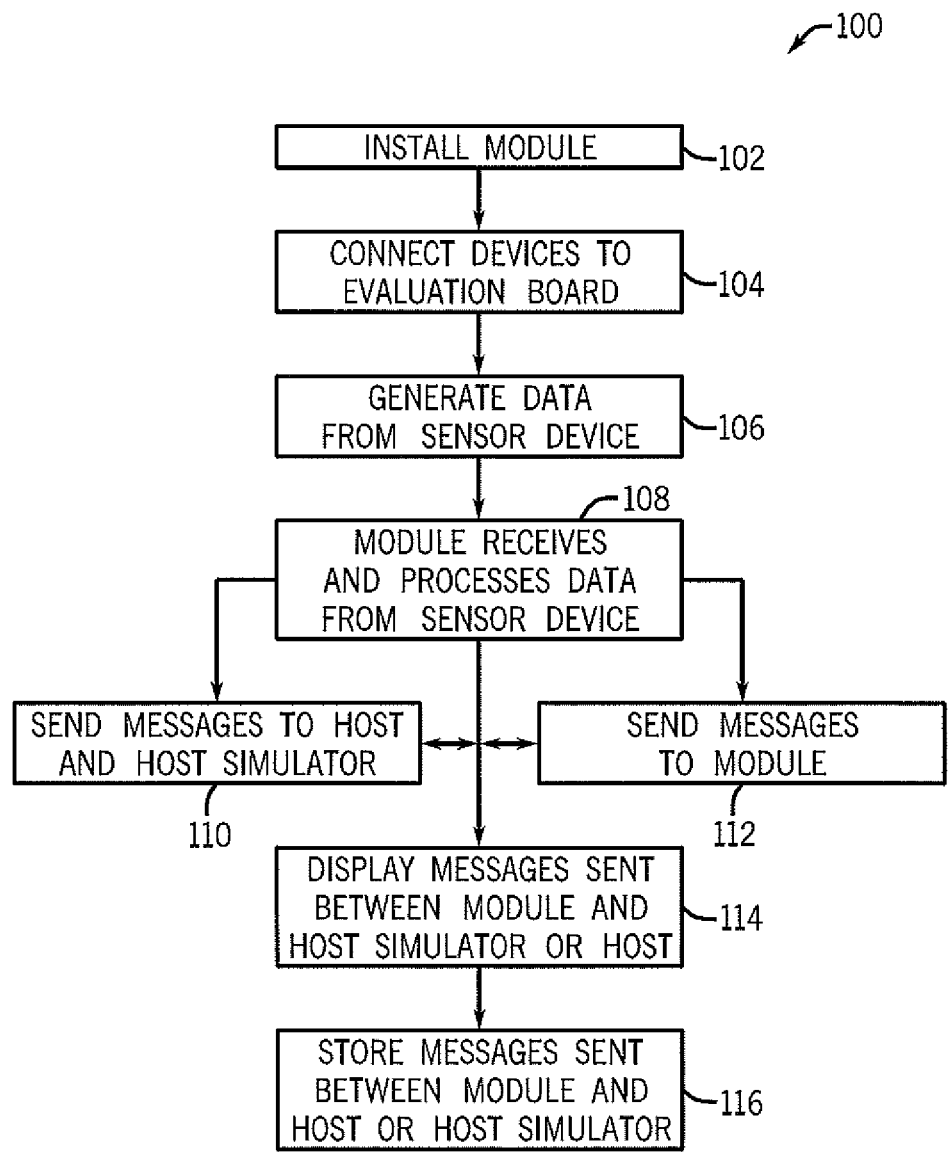
FIG. 6 is a flowchart of a process for use and operation of the evaluation board of FIG. 2 in accordance with an embodiment of the present disclosure.

FIG. 6 depicts a process 100 for use and operation of the evaluation board 40 in accordance with an embodiment of the present disclosure. The process 100 may depict use and operation of the evaluation board 40 in any of the configurations described above in FIG. 3-5. As described above, depending on the configuration, the evaluation board 40 may communicate with multiple devices, such as the first computer 62, the second computer 82, the sensor device 64, and/or a medical monitor 94.

Initially, a user may install the module 15, such as oximetry module or other medical monitoring module, into the module socket 44 of the evaluation board 40 (block 102). Next, a user may connect devices to the evaluation board 40 (block 104). As shown above in FIGS. 3-5, depending on the desired system configuration, a user may connect the sensor device 64, the first computer 62, the second computer 82, and/or the medical monitor 94 to the evaluation board 40 using the connectors 52 described above.

After connection of devices to the evaluation board, the user may begin generating data from the sensor device 64 (block 106). For example, if the sensor device 64 is a sensor, a user may place the sensor on a person and generate data corresponding to physiological parameters of the person detected by the sensor. If the sensor device 64 is a sensor simulator, the user may activate the sensor simulator to simulate generation of detected physiological parameter data. In some embodiments, the user may also configure the host or host simulator 72 to display certain information (e.g., physiological parameter data) or execute certain functionality (e.g., alarms). In such embodiments, creation and configuration of the host simulator 72 may be performed using the host simulator 72 executing on the computer 62.

During operation of the sensor, the module 15 receives data from the sensor device 64, processes the data, and transmits and receives messages to and from the host or host simulator 72 (block 108). As described above, the communication between the module 15 and the host or host simulator 72 may be in specific protocol, such as a proprietary protocol of the manufacturer of the module 15. As discussed above, in one embodiment the module 15 may communicate and format messages in SHIP. Additionally, in some embodiments, the user may send messages to the host and host simulator 72 using the protocol analyzer 70 (block 110). Further, in some embodiments the user may send messages directly to the module 15 from the protocol analyzer 70 or the host simulator 72 (block 112).

During or after operation of the evaluation board 40, a user may display messages sent between the module and the host or host simulator 72 using the protocol analyzer 70 (block 114). For example, the user may view the messages on the display of the computer 62. The protocol analyzer 70 may be configured to display a subset of the available messages sent between the module and host or host simulator 72. For example, if the module 15 communicates using a specific protocol, the protocol analyzer 70 may be configured to only display those protocol messages useful for testing and debugging. Further, the protocol analyzer 70 may be configured to not display messages from the protocol that are undesirable for a user to view. In this manner, only selected messages of a specific protocol may be displayed to a user, without providing a user access to the code defining the protocol.

In some embodiments, as discussed further below, the protocol analyzer 70 may provide processing of messages communicated between the host or host simulator 72 and the module 15, such as by interpreting or filtering such messages. Additionally, the protocol analyzer 70 may store messages sent between the module and the host or host simulator 72 to a log file stored on the memory 66 of the computer 62. As discussed further below, this log file may be viewed or printed by a user, and may be used to playback messages to the module 15.

FIGS. 7-12 are a flowchart and screenshots that depict operation of the protocol analyzer 70. As described further below, the protocol analyzer 70 provides for display of messages sent between the module 15 (either installed in the evaluation board 40 or integrated into a host) and a host (e.g., second computer 82 or monitor 94) or host simulator 72, and to transmit messages to the module 15. Additionally, the protocol analyzer 70 provides filtering, parsing, and logging of such messages.

Figure 7:
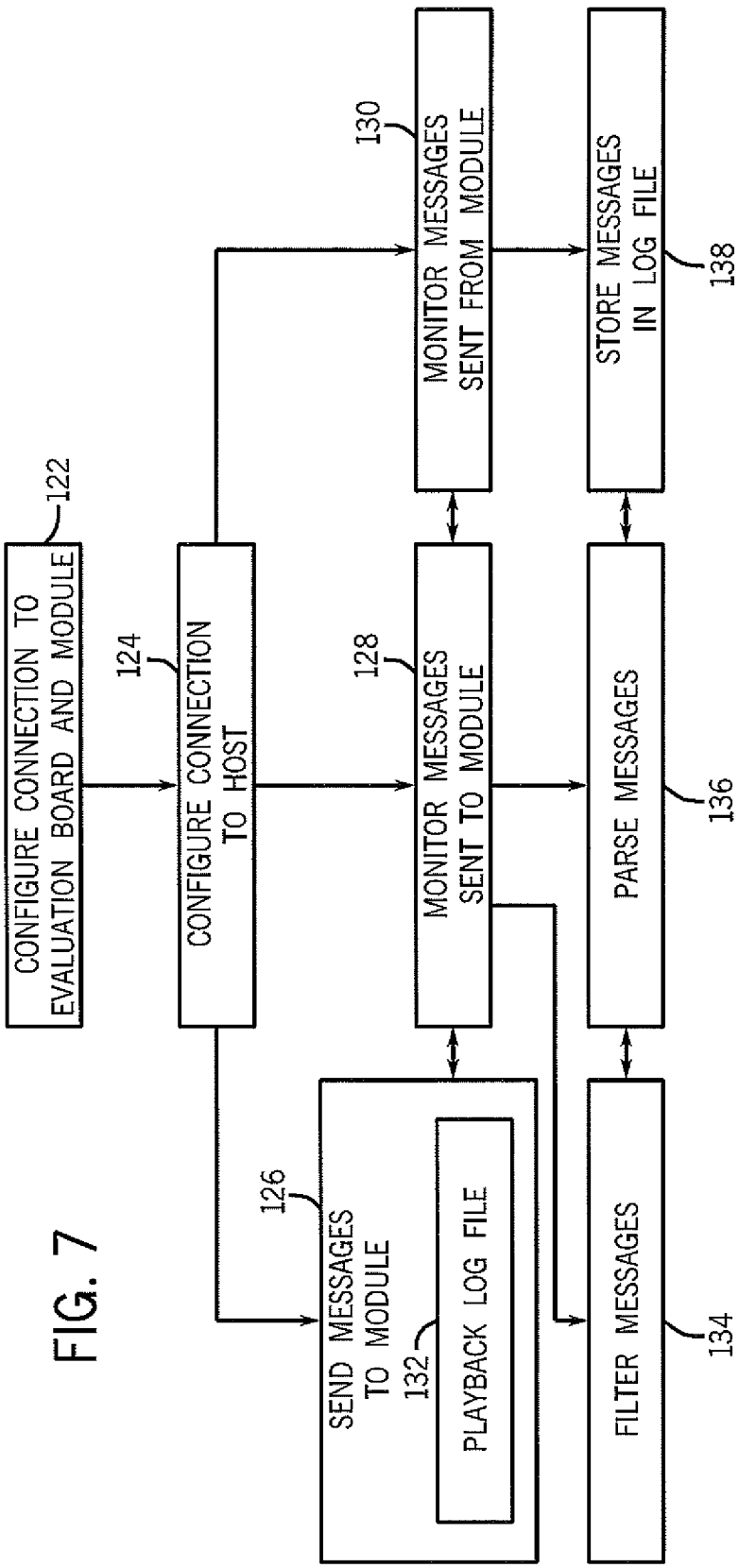
FIG. 7 is a flowchart depicting operation of a protocol analyzer 70 in accordance with an embodiment of the present disclosure.

Turning now to operation of the protocol analyzer 70, FIG. 7 is a flowchart 120 depicting operation of the protocol analyzer 70 in accordance with an embodiment of the present disclosure. Initially, the protocol analyzer 70 may be used to configure connections to the evaluation board 40 and the module 15 (block 122). For example, as discussed above, the computer 62 executing the protocol analyzer 70 may be coupled to the evaluation board 40 by the USB connection 52C. The protocol analyzer 70 may enable configuration of resources of the computer 62 to enable communication to and from the evaluation board 40 (and the module 15) and the computer 62. Additionally, the protocol analyzer 70 may be used to configure a connection to the host (block 124). For example, the protocol analyzer 70 may be configured to connect to the second computer 82 or the medical monitor 94. In some embodiments, as described above, the host simulator 72 may be included on the computer 62 that includes the protocol analyzer 70. In such embodiments, the host simulator 72 may be a part of the protocol analyzer 70, or the protocol analyzer 70 may automatically configured to communicate with the host simulator 72. In other embodiments, the host simulator 72 may execute on a different computer coupled to the evaluation board 40.

The protocol analyzer 70 may be used to transmit messages to the module (block 126), monitor messages sent to the module 15 (block 128), and monitor messages sent from the module 15 (block 130). Any one of or combination of these functions may be used during testing and debug of the host or host simulator 72 and the module 15. If the protocol analyzer 70 is used to transmit messages to the module, the protocol analyzer 70 may also include the capability to playback log files as messages sent to the module (block 132). The log files may include previously stored messages sent to or received from the module 15. A user may playback a log file to determine how the module 15 responds to the messages recorded in the log file.

During or after display of messages sent to and received from the module 15, the protocol analyzer 70 may filter messages based on any specified criteria (block 134). The filtering may include filtering by any specified criteria and may include filtering by pattern found in the content of a message. Additionally, the protocol analyzer 70 may parse messages sent between the module and the host or host simulator 72 (block 136). The parsing may include interpreting messages that have been formatted according to the protocol used between the module and the host or host simulator 72. Additionally, as noted above, the protocol analyzer 70 may enable storing of messages sent between the module and the host or host simulator 72 to a log file (block 138).

Figure 8:
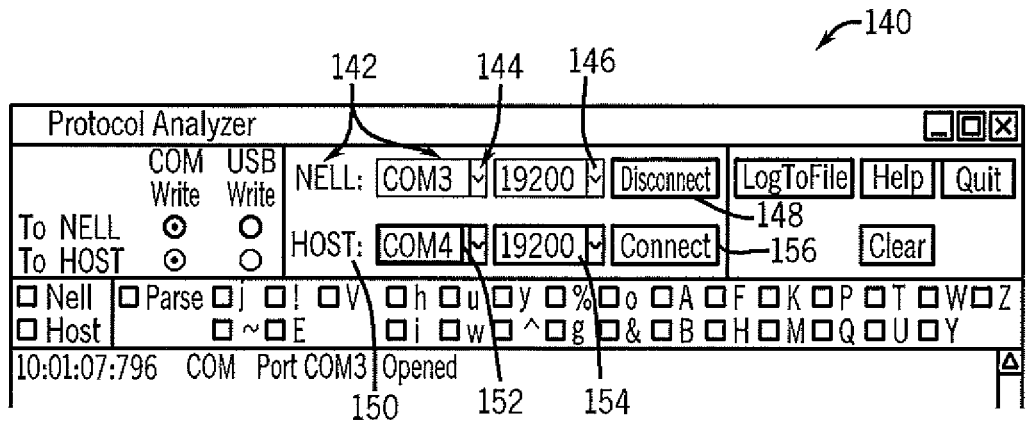
FIGS. 8-12 are screenshots of a protocol analyzer 70 in accordance with an embodiment of the present disclosure.

FIG. 8 is a screenshot of an interface screen 140 of the protocol analyzer 70 in accordance with an embodiment of the present disclosure. FIG. 8 depicts a first set of menus 142 that provide configuration of the connection to the module 15, such as selection of a serial port 144 (e.g., selection of the COM ports available on the computer 62) and selection of a baud rate 146, and a button 148 for initiating or disconnecting the connection to the module 15. Additionally, FIG. 8 also depicts a second set of menus 150 that provide for configuration of connection to the host, such as selection a serial port 152, selection of a baud rate 154, and selection of a button 156 for initiating or disconnecting the connection to the host.

Figure 9:
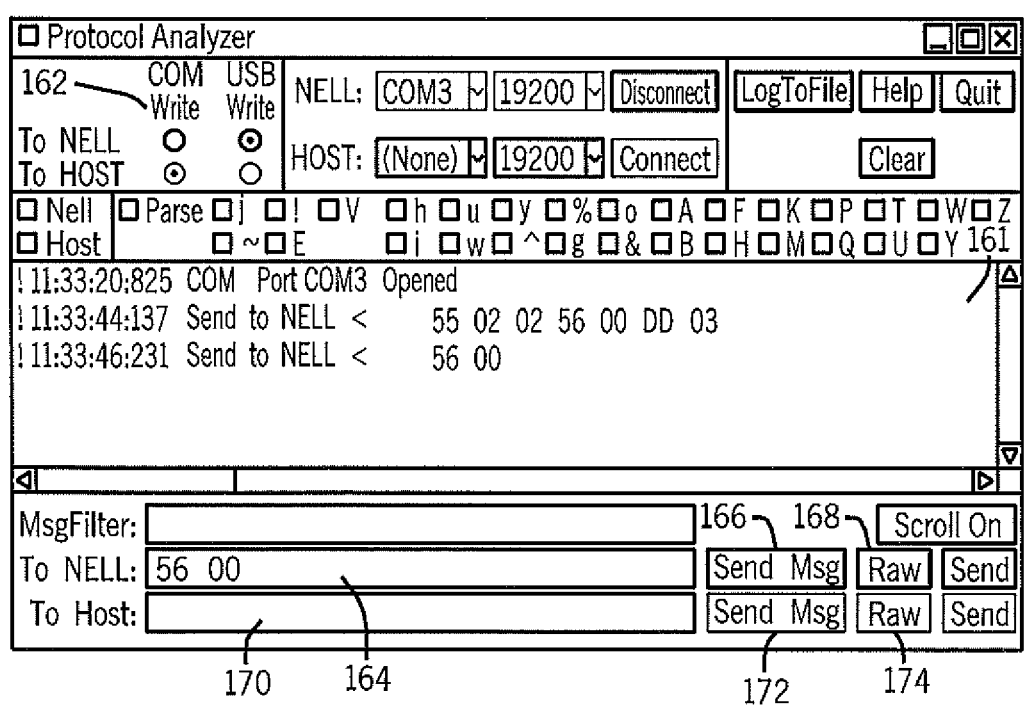

As mentioned above, in some embodiments the protocol analyzer 70 may provide for transmitting of messages to the module 15 and/or to the host or host simulator 72 coupled to the evaluation board 40. FIG. 9 depicts an interface screen 160 illustrating such functionality in accordance with an embodiment of the present disclosure. The interface screen 160 may include a message display area 161 and radio buttons 162 for selection of a write connection. The interface screen 160 includes a dialog box 164 and corresponding "Send Msg" button 166 and "Raw" button 168 for transmitting messages to the module 15. The interface screen 160 also includes a dialog box 170 and corresponding "Send Msg" button 172 and "Raw" button 174 for transmitting messages to the host. For example, as shown in FIG. 9, a user may send messages to the module by entering text "56 00" in the dialog box 164 and selecting the "Send Msg" button 166. The protocol analyzer 70 may format the message according to the protocol used by the module 15 and transmit the message to the module 15. The message display area 161 may display the results of the send action and the formatted message (e.g., the contents of the protocol packet) sent to the module 15. A user may also send unformatted messages (i.e. messages not formatted to any protocol) of the text in the dialog box 164 by selecting the "Raw" button 168. Similarly, a user may send formatted and unformatted messages to the host using the "Send Msg" button 172 and the "Raw" button 170.

Figure 10:
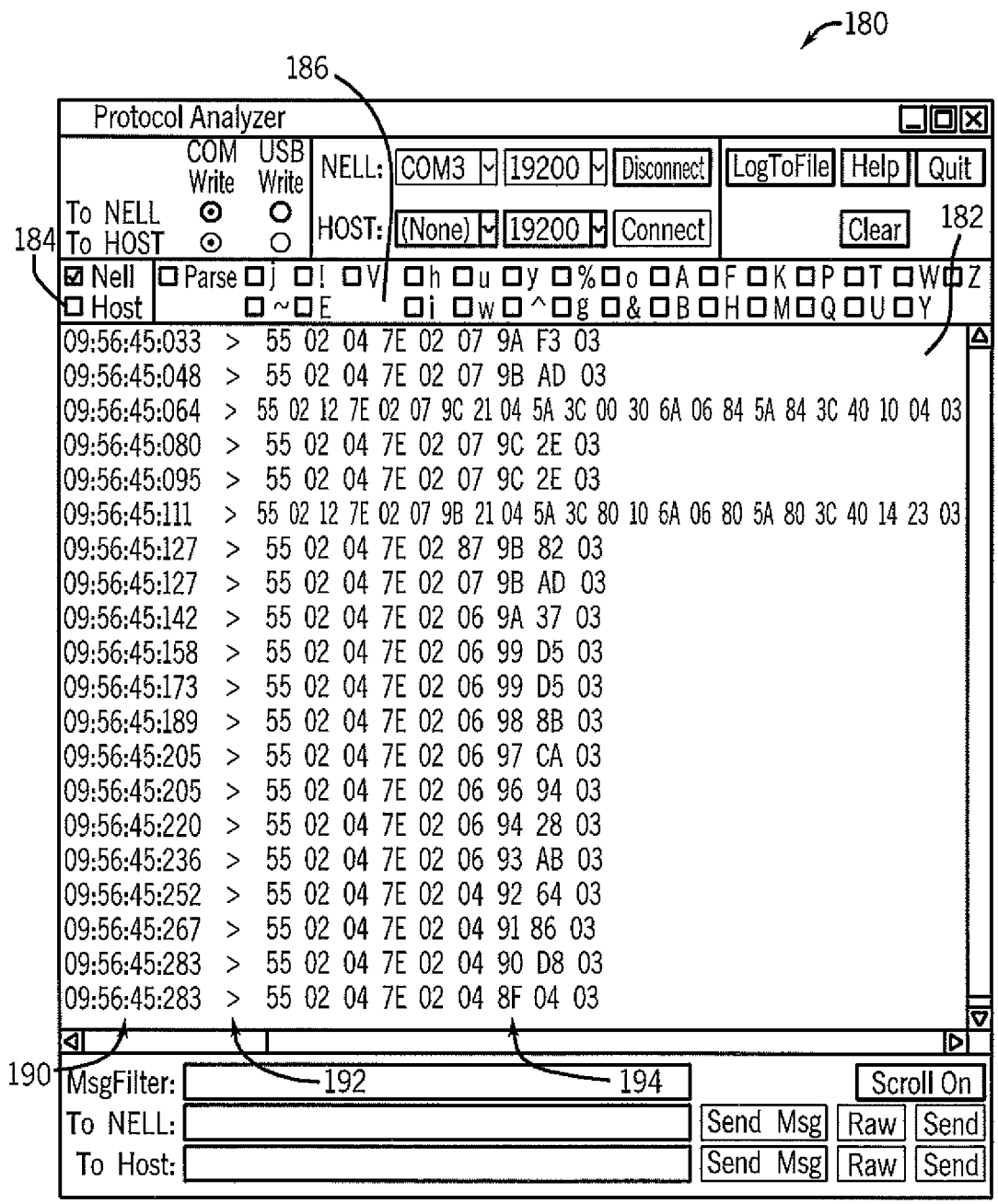

FIG. 10 depicts an interface screen 180 of the protocol analyzer 70 illustrating monitoring of messages sent between the module and the host (or host simulator 72) in accordance with an embodiment of the present disclosure. A display area 182 of the interface screen 180 may display the messages sent between the module and the host. Additionally, a user may filter the messages displayed by selecting items from a first set of checkboxes 184 and a second set of checkboxes 186. The first set of checkboxes 182 may enable a user to select display of all messages sent from the module 15 and/or messages sent from the host. The second set of checkboxes 186 may enable a user to select display of messages that only contain the selected message key (e.g., "V", "E", "!", etc. as shown in FIG. 10). The display area 182 may display the time (column 190, also referred to as the "timestamp") of the message (or, additionally, the date of the message), the direction (column 192) of the message, and the contents (column 194) of the message.

Figure 11:
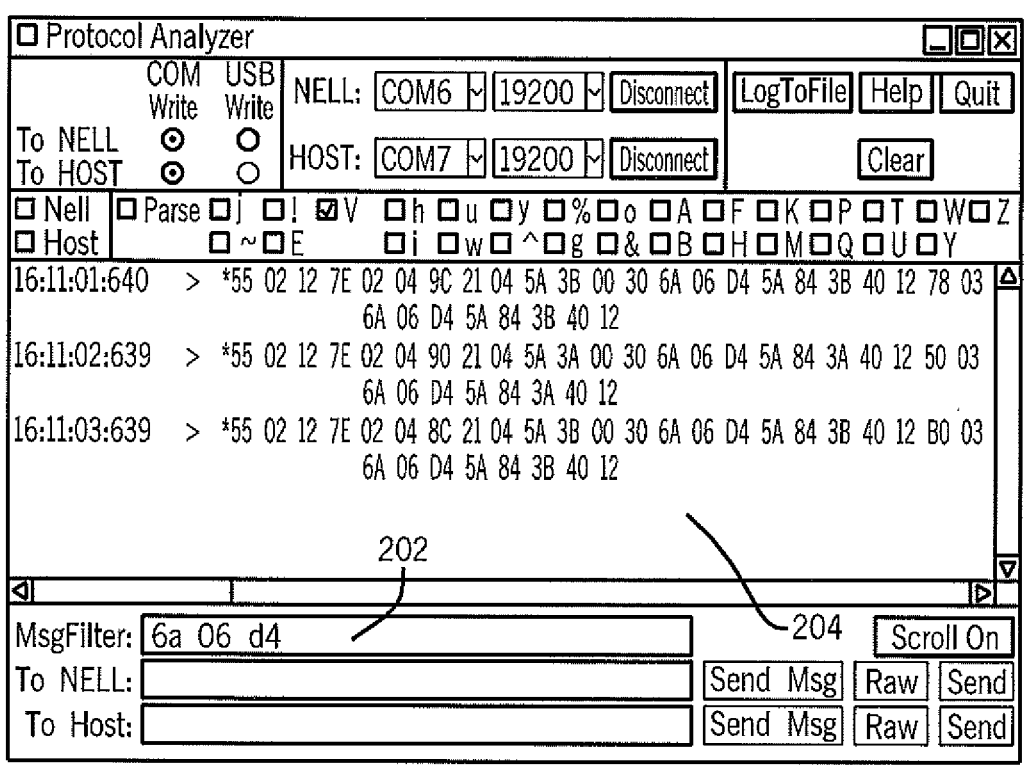

FIG. 11 depicts an interface screen 200 of the protocol analyzer 70 illustrating filtering of messages in accordance with an embodiment of the present disclosure. The interface screen 200 includes a "MsgFilter" dialog box 202 that enables a user to filter messages based on text entered in the dialog box 202. The display area 204 of the interface screen 202 shows the messages having content that matches the specified sequence entered in the dialog box 202. For example, each message shown in the display are 204 includes the sequence "6a 06 d4" entered in the "MsgFilter" dialog box 202.

Figure 12:
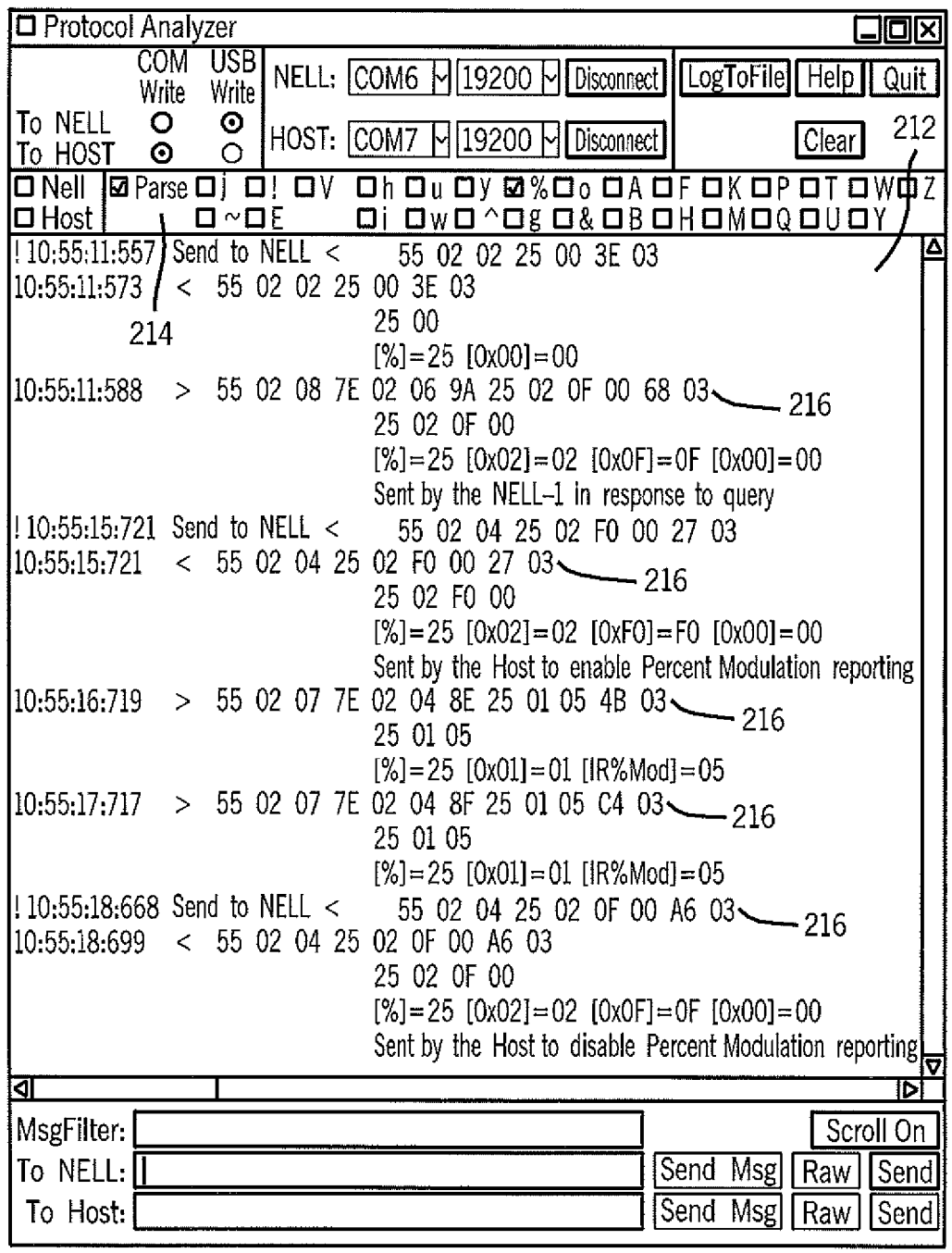

FIG. 12 depicts an interface screen 210 depicting parsing of messages by the protocol analyzer 70 in accordance with an embodiment of the present disclosure. The contents of monitored messages and the parsed output may be displayed in a display area 212 of the interface screen 210. The parsing functionality may be activated by selecting a checkbox 214. After activating message parsing, the protocol analyzer 70 may parse the message contents 216 and display text 218 corresponding to the contents of the message. In some embodiments, the protocol analyzer 70 may include a lookup table, database, or other storage component that stores text corresponding to different message contents for the protocol used by the module 15.

Figure 13:
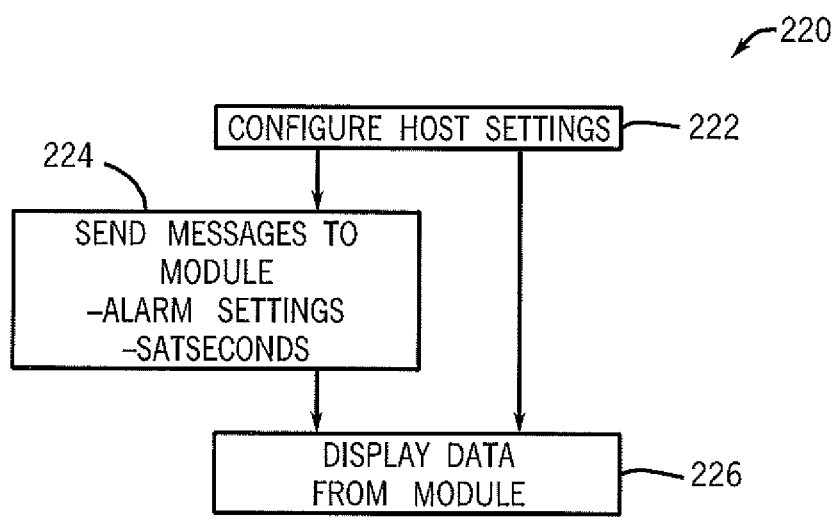
FIG. 13 is a flowchart depicting operation of a host simulator 72 in accordance with an embodiment of the present disclosure.

Turning now to the host simulator 72, FIG. 13 is a flowchart 220 depicting operation of the host simulator 72 in accordance with an embodiment of the present disclosure. As described above, the host simulator 72 may execute on the computer 62 that is coupled to the evaluation board 40. The host simulator 72 provides a simulated host to allow a user to monitor, test, and debug messages sent between the simulated host and the module 15, without using a software host on another computer or a hardware host.

Initially, a user may configure settings for the host simulator 72 (block 222). The configuration may include selecting the connection to the evaluation board 40 (and the module 15) and configuring display settings. As also described above, the host simulator 72 may be used to transmit messages directly to the module (block 224). The user may select any number and/or type of messages to send to the module. Additionally, the host simulator 72 may provide for a "query" function to query the module 15 and receive the settings from the module 15. In some embodiments, such messages may include alarm settings (e.g., SpO2 high and low settings, pulse rate high and low settings, etc.), enabling and disabling sensor adjust messages, and/or any other settings stored, used, and/or accessible by the module. Additionally, the host simulator 72 displays data from the module (block 226), such as would be displayed on a hardware host (e.g., a medical monitor).

Figure 14:
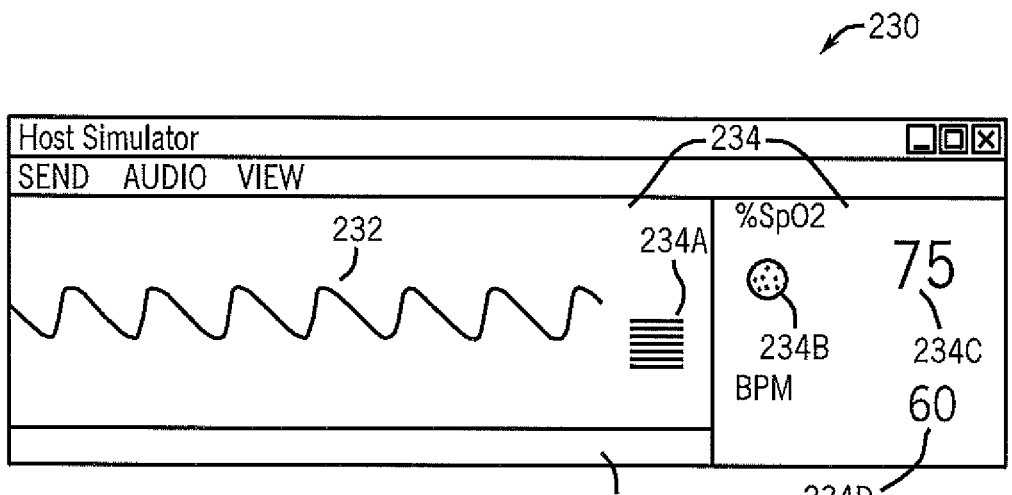
FIG. 14 is a screenshot of a host simulator 72 in accordance with an embodiment of the present disclosure.

FIG. 14 depicts a display screen 230 of the host simulator 72 in accordance with an embodiment of the present disclosure. The display screen 230 simulates the display screen of a hardware host (e.g., a medical monitor) such that the host simulator 72 allows a user to view changes of a host display in response to the messages received from and sent to the module 15. The display screen 230 may include display of a waveform 232 (e.g., a plethysmographic waveform) that corresponds to the physiological parameter measured or simulated by the sensor device 64 after processing by the module. The display screen 230 may also include additional graphical or numeric displays 234 that also display data processed by the module 15. Some or all of the graphical or numeric displays 234 may correspond to data received from the sensor device and processed by the module 15 (such as data corresponding to a physiological parameter), and/or data stored in or generated by the module in response to messages sent from the protocol analyzer 70 or the host simulator 72 (such as alarm data). For example, as shown in FIG. 14, the graphical displays may include a blip display 234A, an alarm display (such as a SatSeconds® display 234B), an SpO2 indicator 234C, a beats-per-minute (BPM) indicator 234D, and display area for other messages 234E (e.g., alarm messages, sensor adjust messages, etc.).

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A device, comprising:
   a printed circuit board assembly configured to facilitate development of a host medical device, the printed circuit board comprising:
      a socket configured to receive a medical monitoring module;
      a standardized connection configured to facilitate the transfer of data from the medical monitoring module to a general purpose computer that is configured to emulate the host medical device;
      a medical sensor connection configured to couple a sensor device to the medical monitoring module; and
      an isolated power supply configured to supply power to the socket.

2. The device of claim 1, wherein the standardized connection comprises a universal serial bus connection or a serial communications port.

3. The device of claim 1, wherein the medical monitoring module comprises a pulse oximetry module.

4. The device of claim 1, wherein the medical sensor connection is configured to couple to a pulse oximetry sensor or an ECG sensor.

5. The device of claim 1, wherein the sensor device comprises a sensor simulator.

6. A method for testing a medical monitoring module to facilitate development of a host medical device, comprising:
   receiving data from a sensor device coupled to an evaluation board;

providing the data to the medical monitoring module coupled to the evaluation board; and sending data in a first protocol from the medical monitoring module to a device coupled to the evaluation board, wherein the device comprises a general purpose computer that is configured to emulate the host medical device during the testing of the medical monitoring module.

7. The method of claim 6, wherein the device comprises a protocol analyzer configured to display the data sent by the medical monitoring module to the device.

8. The method of claim 6, comprising receiving data from a medical monitor coupled to the evaluation board.

9. The method of claim 6, wherein the medical monitoring module comprises a pulse oximetry module.

10. The method of claim 6, wherein the sensor device comprises a sensor simulator.

11. The method of claim 6, wherein the sensor device comprises a pulse oximetry sensor.

12. The method of claim 6, comprising generating the data from the sensor device.

13. The method of claim 12, wherein generating the data from the sensor device comprises generating simulated physiological parameter data.

14. An evaluation board for testing a medical monitoring module to facilitate development of a host medical device, the evaluation board comprising:

a socket configured to receive the medical monitoring module; and a standardized connection configured to couple to a computer comprising a host simulator emulating the host medical device;

wherein the evaluation board provides routing of messages between the medical monitoring module and the computer during the testing of the medical monitoring module.

15. The evaluation board of claim 14, comprising an isolated power supply configured to provide power to the medical monitoring module.

16. The evaluation board of claim 14, comprising a non-isolated power supply to provide power to the standardized connection.

17. The evaluation board of claim 14, wherein the medical monitoring module comprises a pulse oximetry module.

18. The evaluation board of claim 17, comprising a medical sensor connector configured to coupled to a sensor device.

19. The evaluation board of claim 18, wherein the sensor device comprises a sensor simulator configured to simulate monitoring of a physiological parameter.

20. The evaluation board of claim 18, wherein the sensor device comprises a pulse oximetry sensor.

\* \* \* \* \*